(12) United States Patent
Yabusaki (10) Patent No.: US 8,211,651 B2
(45) Date of Patent: Jul. 3, 2012

(54) METHOD FOR MEASURING ENDOTOXIN AND REAGENT KIT FOR MEASURING ENDOTOXIN

(75) Inventor: Katsumi Yabusaki, Chofu (JP)

(73) Assignee: Kowa Company, Ltd., Nagoya-shi, Aichi (JP)

( * ) Notice: Subject to any disclaimer, the term of this patent is extended or adjusted under 35 U.S.C. 154(b) by 52 days.

(21) Appl. No.: 12/809,337

(22) PCT Filed: Dec. 18, 2008

(86) PCT No.: PCT/JP2008/073101
§ 371 (c)(1),
(2), (4) Date: Jun. 18, 2010

(87) PCT Pub. No.: WO2009/078465
PCT Pub. Date: Jun. 25, 2009

(65) Prior Publication Data
US 2011/0201015 A1 Aug. 18, 2011

(30) Foreign Application Priority Data
Dec. 19, 2007 (JP) ................................. 2007-327784

(51) Int. Cl.
*G01N 33/53* (2006.01)
(52) U.S. Cl. ........................... 435/7.1; 435/7.2; 436/518
(58) Field of Classification Search ........................ None
See application file for complete search history.

(56) References Cited

U.S. PATENT DOCUMENTS

| 5,316,911 A | 5/1994 | Baek et al. |
| 5,550,030 A | 8/1996 | Tanaka et al. |
| 5,591,628 A | 1/1997 | Bæk et al. |
| 6,645,724 B1 * | 11/2003 | Ding et al. ..................... 435/7.1 |

FOREIGN PATENT DOCUMENTS

| EP | 2 081 024 | 7/2009 |
| JP | 06-130064 | 5/1994 |
| JP | 2003-322655 | 11/2003 |

OTHER PUBLICATIONS

International Search Report dated Feb. 3, 2009 issued to international application No. PCT/JP2008/073101.

* cited by examiner

*Primary Examiner* — Jacob Cheu
(74) *Attorney, Agent, or Firm* — Knobbe, Martens, Olson & Bear, LLP (57) ABSTRACT

A technique which is less likely to be affected by turbid or color of samples and with which prompt and simple detection or concentration measurement of endotoxin can be achieved is provided. A reagent in which proteins contained in LAL are adsorbed or bound onto fine particles dispersed in a previously prepared drug liquid is prepared, and this reagent and a sample containing endotoxin are mixed. By doing this, endotoxin acts on the proteins on the fine particles and the fine particles are associated with one another to form a large aggregate at an early stage. By optically measuring the formation of this aggregate, detection or concentration measurement of endotoxin is performed.

10 Claims, 4 Drawing Sheets

METHOD FOR MEASURING ENDOTOXIN AND REAGENT KIT FOR MEASURING ENDOTOXIN

CROSS-REFERENCE TO RELATED APPLICATIONS

This application is the U.S. National Phase under 35 U.S.C. §371 of International Application PCT/JP2008/073101, filed Dec. 18, 2008, which was published in a non-English language, which claims priority to JP Application No. 2007-327784, filed Dec. 19, 2007.

TECHNICAL FIELD

The present invention relates to a method of detecting endotoxin or measuring the concentration of endotoxin and to a reagent kit to be used for detecting endotoxin or measuring the concentration of endotoxin.

BACKGROUND ART

Endotoxin is a lipopolysaccharide present in a cell wall of a Gram-negative bacterium and is the most typical pyrogen. If a transfusion, a medicine for injection, or blood contaminated with endotoxin is introduced into the human body, endotoxin may induce severe side effects such as fever and shock. Therefore, it has been required that the above-mentioned medicine or instrument is kept not to be contaminated with endotoxin.

A limulus amoebocyte lysate (hereinafter, also referred to as "LAL") contains serine proteases which are activated by endotoxin. In the case where LAL reacts with endotoxin, a coagulogen present in LAL is hydrolyzed into a coagulin by an enzyme cascade of the serine proteases activated depending on the amount of endotoxin, and the coagulin is associated with one another to form an insoluble gel.

Examples of a method of measuring the concentration of endotoxin include a semi-quantitative gelation method which includes: leaving a sample blended with LAL to stand; turning the container upside down after a lapse of a predetermined time; and judging whether the sample gets gelation or not based on the presence or absence of dropping of the sample to examine whether or not the sample contains endotoxin above a certain concentration. Examples of another sensitive method of quantifying endotoxin include: a turbidimetric method which analyze a sample with time by determining the turbidity of a sample caused by gel formation by a reaction between LAL and endotoxin; and a colorimetric method which is performed by using a synthetic substrate which is hydrolyzed by an enzyme cascade to develop a color.

Of the above-mentioned quantification methods, the turbidimetric method may require a very long reaction time until gel formation is detected because the amount of an enzyme activated by an action of a low concentration of endotoxin is small. On the other hand, the colorimetric method has a disadvantage that the method is easily affected by the turbidity (such as blood lipid) of a sample and a pigment mixed (such as hemoglobin caused by hemolysis). Therefore, the above-mentioned turbidimetric method and colorimetric method are not necessarily the best methods for measurement of endotoxin in blood of a patient in emergency or for measurement of endotoxin in a dialysis solution or blood in artificial dialysis.

Moreover, it has been proposed a laser light scattering particle measurement method, which involves measuring formation of fine gel-particles at an aggregation early stage by: forming fine gel-particles at an early stage by stirring a sample obtained by blending LAL and endotoxin; and analyzing the sizes and number of the fine gel-particles based on the intensity of laser light scattered by the fine gel-particles. It has been reported that the method can shorten the measurement time to about one-third compared with the turbidimetric method and can reduce the effects of the turbidity or color of the sample.

However, even if the above-mentioned laser light scattering particle measurement method is used, it takes a time of 40 to 50 minutes to measure a low concentration (about 1 EU (endotoxin unit)/L) of endotoxin. In the laser light scattering particle measurement method, the optical system is complex because particles in a minute space are observed, resulting in a disadvantage that measurement of many analytes is difficult.

Patent Document 1: JP 2667695 B2

DISCLOSURE OF THE INVENTION

Problem to be Solved by the Invention

The present invention has been made in consideration of the above-mentioned problems. An object of the present invention is to provide a technology which is less likely to be affected by the turbidity or color of a sample and with which rapid and simple detection or concentration measurement of endotoxin can be achieved.

Means for Solving the Problems

The most distinctive feature of the method of measuring endotoxin according to the present invention is as follows. That is, a reagent is prepared by adsorbing or binding proteins in LAL to previously prepared fine particles dispersed in a drug solution. Then, a sample containing endotoxin is allowed to act on the reagent, and the fine particles are associated with one another to form a large aggregate at an early stage. By detecting the formation of this aggregate, measurement of endotoxin is performed.

To be specific, the method according to the present invention is a method of measuring endotoxin for detecting endotoxin in a sample or measuring the concentration of endotoxin in a sample, including:

binding or adsorbing a predetermined protein in a limulus amoebocyte lysate to surfaces of fine particles capable of dispersing in a reagent;

blending a reagent where the fine particles to which the predetermined protein is bound or adsorbed are dispersed with a sample; and detecting formation of a gel in the blended solution of the reagent and the sample to detect endotoxin or measuring the degree of formation of the gel to measure the concentration of endotoxin.

The inventors of the present invention have made intensive studies and found that a protein in LAL is bound or adsorbed to fine particles made from resin for example and then allowed to act on endotoxin, larger aggregates are formed at an early stage compared with the case where a sample containing endotoxin is allowed to act on LAL itself. This is caused by hydrolyzing a coagulogen on the fine particles by the enzyme cascade in LAL into a coagulin, which causes association of the fine particles. The inventors have clarified that the aggregation reaction is less likely to be affected by the turbidity or color of the sample and that the aggregation reaction is very stronger than that caused by LAL itself.

In the present invention, based on such phenomenon, a reagent is prepared by binding or adsorbing a protein in LAL to fine particles, and a sample containing endotoxin is allowed to act on the reagent (hereinafter, also referred to as "LAL reagent") to form a large aggregate at an early stage by association of the fine particles, resulting in promoting gel formation in the blended solution of the LAL reagent and the sample. This enables reducing the effects of the turbidity or color of the sample in detection or concentration measurement of endotoxin (hereinafter, collectively referred to as "measurement of endotoxin") and performing the detection or concentration measurement rapidly and simply.

Note that, the above-mentioned predetermined protein has an ability to react with endotoxin to form a gel and includes at least a coagulogen. In addition, the protein may include other proteins such as serine proteases. In the present invention, gel formation means a phenomenon which includes at least one of formation of an aggregate by association of the fine particles, formation of gel particles by association of a coagulin which is not bound or adsorbed to the fine particles, and gel formation of a blended solution of the LAL reagent and a sample.

Meanwhile, in the present invention, the degree of gel formation means an increase in the size or number of an aggregate formed by association of the fine particles as described above, and a gel particle formed by association of the coagulin which is not bound or adsorbed to the fine particles. Alternatively, the degree means changes in physical and chemical properties (e.g., turbidity) caused by gel formation of the blended solution of the LAL reagent and the sample.

The above-mentioned predetermined protein may be a coagulogen purified from the limulus amoebocyte lysate.

As described above, in the aggregation reaction when endotoxin is allowed to act on LAL, the coagulogen is hydrolyzed into the coagulin by the enzyme cascade in LAL, and the coagulin causes association of the fine particles. Therefore, if only the coagulogen previously extracted by purifying proteins in LAL is bound or adsorbed to the fine particles, the fine particles can be associated with one another in a more efficient manner to form an aggregate at more early stage.

In the present invention, in the case where the above-mentioned predetermined protein includes the serine protease and coagulogen, an inhibitor which inhibits a reaction between the serine protease and endotoxin may be added to the reagent, where the fine particles to which the predetermined protein is bound or adsorbed are dispersed, in the process of reagent preparation.

To bind or adsorb the proteins in LAL to the fine particles, first, a functional group capable of binding or adsorbing the proteins is allowed to be present on the surfaces of the fine particles. Then, in such state, the LAL reagent is allowed to act on the functional group to chemically bind or to electrostatically, hydrophilically, or hydrophobically adsorb the proteins to the surfaces of the fine particles. In this case, it takes a long period of time to perform the binding or adsorbing reaction between the proteins in LAL and the fine particles. Therefore, endotoxin which is mixed in a minute amount in the fine particles, reagents used, or water may react with the serine protease in the proteins to hydrolyze the coagulogen into the coagulin, which may start aggregation of the fine particles. In this case, the coagulogen in the reagent may be hydrolyzed and consumed by activation of the enzyme.

In order to solve this problem, in the present invention, in the case where the above-mentioned predetermined protein includes the serine protease and coagulogen, an inhibitor which inhibits a reaction between the serine protease and endotoxin is added to the reagent, where the above-mentioned fine particles to which the predetermined protein is bound or adsorbed are dispersed. This can inhibit aggregation of the fine particles in the process of reagent preparation and can inhibit hydrolysis and consumption of the coagulogen due to activation of the enzyme.

Specifically, the above-mentioned inhibitor may be iron ion or aluminum ion which is known to have an effect of deactivating endotoxin. Alternatively, the inhibitor may be an enzyme inhibitor which prevents activation of the serine protease in LAL.

In addition, in the present invention, the reagent where the fine particles to which the above-mentioned predetermined protein is bound or adsorbed are dispersed may be further mixed with the limulus amoebocyte lysate, and the reagent may be blended with the sample simultaneously with or after the mixing.

This can supplement proteins in LAL to the reagent where the fine particles to which protein is bound or adsorbed are dispersed. By doing this, when the reagent is blended with a sample containing endotoxin, endotoxin can act on the serine protease in the reagent more accurately to hydrolyze the coagulogen bound or adsorbed to the fine particles and the coagulogen in the mixed LAL into the coagulin. As a result, it is possible to more accurately associate the coagulogen bound or adsorbed to the fine particles with one another or to more accurately associate the coagulogen bound or adsorbed to the fine particles with the coagulin in LAL mixed, resulting in promoting formation of an aggregate mainly containing the fine particles. This enables rapid measurement of endotoxin.

This has an advantage in the case where only the coagulogen previously extracted by purifying proteins in LAL is bound or adsorbed to the fine particles, or in the case where an inhibitor which inhibits the reaction of the serine protease and endotoxin in the reagent in the process of reagent preparation is added. That is, even in such case, when the reagent is blended with the sample containing endotoxin, endotoxin can act on the serine protease more accurately.

Note that, in the above-mentioned process, the reagent where the above-mentioned fine particles to which the above-mentioned predetermined protein is bound or adsorbed are dispersed is further mixed with the limulus amoebocyte lysate, and then the mixture is blended with the sample containing endotoxin. The blending may be performed after or simultaneously with the mixing with the lysate. However, to uniformly disperse the coagulogen and serine protease supplemented in the reagent, blending with the sample containing endotoxin is desirably performed after a lapse of a predetermined time from mixing of the reagent with the lysate.

In addition, the present invention may provide a reagent kit for measurement of endotoxin, prepared by binding or adsorbing a predetermined protein in a limulus amoebocyte lysate to the surfaces of fine particles capable of dispersing in a reagent.

The predetermined protein is one having an ability to react with endotoxin to form a gel and includes at least the coagulogen. In addition, the protein may include another protein such as the serine protease.

Further, in the reagent kit for measurement of endotoxin according to the present invention, the predetermined protein may be a coagulogen purified from the limulus amoebocyte lysate.

Further, in the reagent kit for measurement of endotoxin according to the present invention, the predetermined protein may include a serine protease and a coagulogen, and an inhibitor which inhibits a reaction between the serine protease and the endotoxin may be further added to a reagent where the fine particles to which the predetermined protein is bound or adsorbed are dispersed.

In the case where the predetermined protein in the limulus amoebocyte lysate is bound or adsorbed to the surfaces of fine particles dispersible in a reagent to prepare a reagent kit, as described above, endotoxin which is mixed in a minute amount in the fine particles, reagents used, or water may react with the serine protease in the proteins. In this case, the coagulogen may be hydrolyzed into the coagulin in the process of reagent preparation to start aggregation of the fine particles, resulting in consumption of the coagulogen in the reagent.

In order to solve this problem, in the reagent kit for measurement of endotoxin according to the present invention, in the case where the above-mentioned predetermined protein includes the serine protease and coagulogen, an inhibitor which inhibits the reaction between the serine protease and endotoxin is added to the reagent where the above-mentioned fine particles to which predetermined protein is bound or adsorbed are dispersed. This can inhibit aggregation of the fine particles in the process of reagent preparation and can inhibit hydrolysis and consumption of the coagulogen due to activation of the enzyme. The above-mentioned inhibitor may be iron ion, aluminum ion, or an enzyme inhibitor.

Further, the reagent kit for measurement of endotoxin according to the present invention may be prepared by further mixing the reagent where the fine particles bound or adsorbed to the predetermined protein are dispersed with the limulus amoebocyte lysate.

Note that the above-mentioned means for solving the problems of the present invention may be combined to a maximum extent.

Effects of the Invention

The present invention enables rapid and simple detection or concentration measurement of endotoxin, which is less likely to be affected by the turbidity or color of a sample.

DESCRIPTION OF SYMBOLS 1 bead
2 coagulogen
3 coagulogen
10 LAL-bound bead

Best Mode for Carrying out the Invention

The process of forming a gel by a reaction between LAL and endotoxin has been studied well. That is, when endotoxin is bound to a serine protease, i.e., C-factor in LAL, the C-factor is activated, the activated C-factor hydrolyzes and activates another serine protease, i.e., B-factor in LAL to its activated form. The activated B-factor immediately hydrolyzes a precursor of a clotting enzyme in LAL to clotting enzyme as an activated form, and the clotting enzyme hydrolyzes a coagulogen in LAL to form a coagulin. Further, the formed coagulin is then associated with one another to form an insoluble gel.

A series of reactions as described above are similar to the process of forming a fibrin gel via serine proteases such as Christmas factor or thrombin present in mammals. Such enzyme cascade reactions have a very strong amplification effect because even a very small amount of an activation factor activates the subsequent cascade in a chain reaction. Therefore, according to a method of measuring endotoxin using LAL, it is possible to detect a very small amount (sub-pg/mL order) of endotoxin.

Examples of a measurement method which can quantify endotoxin include the turbidimetric method and the laser light scattering particle measurement method, as described above. In such measurement methods, endotoxin can be measured sensitively by detecting association products of a coagulin formed by the enzyme cascade reactions in LAL as the turbidity of a sample in the former method or as fine gel-particles formed in the system in the latter method.

However, in the turbidimetric method, each coagulin is a fine particle (nanometer order). Therefore, if the particles are progressively associated with one another, the particles cannot be detected as the turbidity until the product grows to a size which can be detected optically. Meanwhile, in the turbidimetric method, in general, a sample is left to stand to form a gel in the whole system. Accordingly, the coagulin collision probability is low, and the association rate is not always high. Therefore, in the turbidimetric method, there is a disadvantage that it takes a very long time before detection or concentration measurement of endotoxin can be achieved.

On the other hand, in the laser light scattering particle measurement method, fine gel-particles formed in the system are directly measured, and hence the method is more sensitive than the turbidimetric method. In addition, gel formation can be detected in a short time compared with the turbidimetric method because in general, a sample containing LAL and an analyte is forcibly stirred.

However, in the laser light scattering particle measurement method, the optical system is complex because particles in a minute space are observed, resulting in a disadvantage that measurement by a simple device is difficult.

The method of measuring endotoxin further includes a colorimetric method. The method does not measure the turbidity of a sample caused by a coagulin gel although the method is based on the enzyme cascade reactions in LAL. The method is performed by measuring absorbance changes caused by a reaction between an analyte and LAL containing a synthetic substrate, which is hydrolyzed by a clotting enzyme to develop a color. In the colorimetric method, the concentration of a chromogenic substance formed in the system is measured, and hence a low concentration of endotoxin can be measured in a short time compared with the turbidimetric method or laser light scattering particle measurement method, where gel formation in a sample is measured.

However, a synthetic chromogenic substrate has an absorbance peak at about 405 to 410 nm, and the wavelength overlaps with the absorbance peak of hemoglobin (410 nm) which is mixed in a sample and is generated by hemolysis. A white scatter in blood, such as chyle, scatters more actively in the case where the light wavelength is shorter, and hence a light having a wavelength on the shortest side (purple) in the visible light region including the absorbance peak of the synthetic chromogenic substrate is particularly affected by the white scatter. As described above, the colorimetric method can be performed in a very short time but has a problem with accuracy of measurement of an analyte mainly containing blood.

An object of the present invention is to reduce the effect of the turbidity or color of a sample on measurement. Therefore, the present invention employs not a method where a synthetic chromogenic substrate is used, such as the colorimetric method, but a process of coagulin formation caused by the enzyme cascade in LAL. A further object of the present invention is to develop a measurement technique which is similar to the turbidimetric method but can be performed in a short time compared with the laser light scattering particle measurement method and is performed using an apparatus which can be made easily. Therefore, the present invention does not employ a method performed by passively waiting for hydrolysis of a coagulogen into a coagulin and a progressive aggregation process, which are caused by the enzyme cascade in LAL.

Hereinafter, best modes for carrying out this invention are described illustratively in detail with reference to drawings.

EXAMPLE 1

In this example, a coagulogen is preliminarily bound to the surfaces of fine particles with a size which can be detected by the turbidimetric method or the laser light scattering particle measurement method or is slightly smaller than a detection limit size. Then, a sample containing endotoxin is blended in a reagent prepared by mixing the particles with a LAL reagent. By doing this, a coagulin formed in LAL is associated with a coagulin formed on the fine particles, or coagulins formed on the fine particles are associated with one another, to thereby form a large aggregate with a size which can be detected by the turbidimetric method or the laser light scattering particle measurement method in short time. As a result, endotoxin can be measured more rapidly by the turbidimetric method or the laser light scattering particle measurement method.

Figure 1:
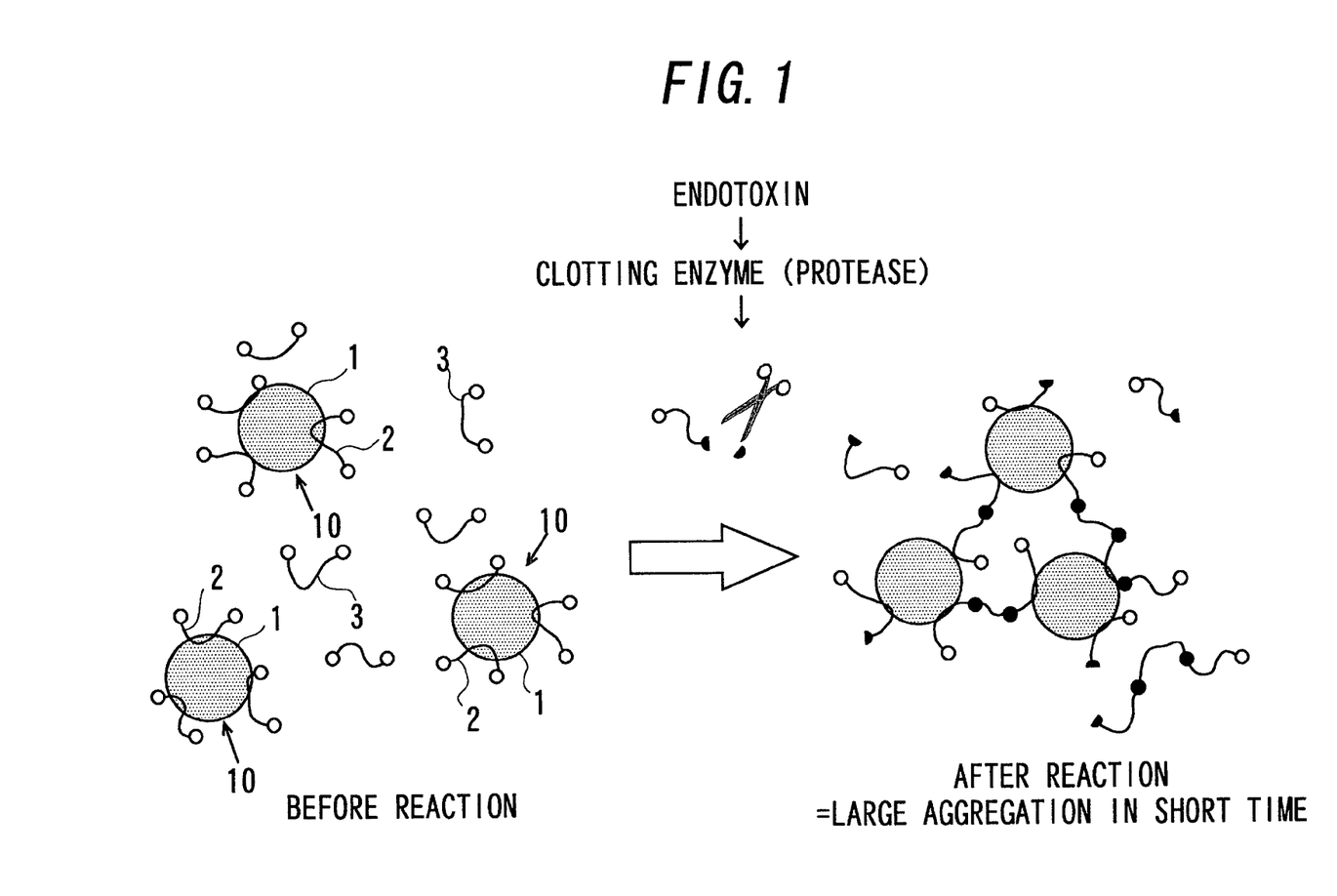
FIG. 1 is a drawing illustrating an aggregation mechanism of LAL-bound beads in examples of the present invention.

FIG. 1 illustrates an aggregation mechanism of the fine particles according to this example. In FIG. 1, the drawing on the left side of the central arrow is a schematic view of the reagent before the reaction with endotoxin. The drawing on the right side of the arrow is a schematic view of the reagent after the reaction with endotoxin.

As shown in FIG. 1, before the reaction, the beads 1, which are fine particles in this example, the coagulogens 2 which are bound to the surfaces of the fine particles, and the coagulogens 3 which are not bound to the surfaces of the fine particles are dispersed. Note that, hereinafter, as a matter of convenience, fine particles obtained by binding the coagulogens 2 to the beads 1 are referred to as LAL-bound beads 10.

As the bead 1 which serves as a carrier for binding the coagulogen 2, there is selected a bead which can adsorb, support, or bind the coagulogen 2 contained in a protein in LAL, can be dispersed uniformly in a reaction system, and does not prevent or promote a process of gel formation by endotoxin. The material of the bead 1 is not particularly limited, and examples thereof include polystyrene latex resin, silica, silicon resin, cellulose resin, polyvinyl alcohol resin, and hydroxyapatite. The polystyrene latex resin, silica, and cellulose resin are desirable.

The size of the bead 1 used is within a range of 0.05 µm to 50 µm in view of a condition where the bead can be detected optically at an early stage by aggregation, ease of handling in preparation, dispersibility in a system, etc. The size is more desirably within a range of 0.1 µm to 30 µm. The coagulogen 2 can be bound to the surface of the bead 1 by a method of adsorbing the coagulogen 2 electrostatically, hydrophilically, or hydrophobically, or by a method of binding the coagulogen 2 chemically.

To adsorb the coagulogen 2 electrostatically, hydrophilically, or hydrophobically to the bead 1, the surface of the bead 1 must have a functional group capable of supporting the coagulogen 2. Examples of the functional group include an amino group, a carboxyl group, a phosphate group, a hydroxyl group, a sulfonate group, a thiol group, an alcohol group, and an alkyl group.

On the other hand, in the case where the coagulogen 2 is bound chemically to the surface of the bead 1, the bead must have a functional group capable of chemically binding to an amino group, a carboxyl group, a thiol group, or the like in a side chain of the coagulogen 2. Examples of the functional group include a carboxyl group, an amino group, a vinyl group, an epoxy group, a styryl group, a methacryloxy group, an acryloxy group, an ureido group, a thiol group, a sulfide group, an isocyanate group, and an isothiocyanate group.

The LAL reagent or a coagulogen prepared and purified from the LAL reagent or the like is allowed to act on the bead 1 such as the polystyrene latex resin, silica, silicon resin, cellulose resin, polyvinyl alcohol resin, or hydroxyapatite having the above-mentioned functional groups on its surface. By doing this, the coagulogen 2 is electrostatically, hydrophilically, or hydrophobically adsorbed or supported to the surface of the bead 1. Alternatively, a reactive functional group on the bead 1 is chemically bound to the coagulogen 2 via an amino group, a carboxyl group, or a thiol group in the coagulogen 2. According to this process, the LAL-bound bead 10 can be prepared.

The reaction temperature and reaction time in the above-mentioned process vary whether adsorbing, supporting, or chemical binding is performed. The reaction temperature is desirably 0° C. to 45° C., more desirably 4° C. to 37° C. The reaction time is desirably 10 minutes to 64 hours, more desirably 2 hours to 24 hours. To perform the reaction uniformly, a sample is desirably stirred well during the reaction.

Note that, to adsorb, support, or bind the coagulogen 2 on the bead 1, the coagulogen 2 may be adsorbed, supported, or bound to the bead 1 without selecting a protein in LAL, or the coagulogen 2 may be adsorbed, supported, or bound to the bead 1 after the coagulogen in LAL is purified. In the case of employing the method of adsorbing, supporting, or binding the coagulogen to a fine particle without selecting a protein in LAL, proteins other than the coagulogen 2 are also adsorbed, supported, or bound to the bead 1. However, it is possible to omit a step of purifying the coagulogen in LAL, and hence the cost for preparation and purification of the reagent can be reduced. Note that, in this case, in FIG. 1, large amounts of proteins (not shown) other than the coagulogens 2 and 3 in LAL are present on the bead 1 and in the reagent surrounding the bead 1.

The reaction for adsorbing, supporting, or binding the coagulogen or a protein in LAL to the bead 1 as described above takes much time. Therefore, if a slight amount of endotoxin is mixed in the bead 1 itself, reagents used, water, etc., a clotting enzyme activated by endotoxin mixed therein before completion of preparation of the reagent hydrolyzes the coagulogen to form the coagulin, thereby causing aggregation in the system. To inhibit this, iron ion or aluminum ion, which is known to have an effect of deactivating endotoxin, may be added to the reaction system. The concentration of the iron ion or aluminum ion added in this case is desirably 100 mM or less.

To inhibit activation of serine proteases in LAL, a variety of enzyme inhibitors may be added. Examples of the enzyme inhibitors include Diisopropylfluorophosphate, Benzamidine, Phenylmethanesulfonyl fluoride, 4-(2-Aminoethyl)-benzenesulfonyl fluoride, 6-Amidino-2-naphthyl-4-guanidinobenzoatedimethanesulfonate, p-Amidinophenylmethylsulfonyl fluoride, Aprotinin, Antipain, Leupeptin, Ecotin, PPACK (Phe-Pro-Arg-chloromethylketone), $\alpha$2-Macroglobulin, and Trypsin inhibitor. The concentration of each of such enzyme inhibitors is desirably 100 mM or less. The concentration is further desirably 20 mM or less.

In this state, the LAL-bound beads 10 may be dispersed completely independently. In addition, in part or all of the LAL-bound beads 10, a plurality of the beads may be crosslinked by the effect of adsorption, support, or chemical binding. The thus-prepared LAL-bound beads 10 are washed with purified water or physiological saline not containing endotoxin to remove excess proteins or coagulogens in LAL, which do not bind to the beads 1, and an additive such as iron ion, aluminum ion and an enzyme inhibitor. Finally, the LAL-bound beads 10 are resuspended before use in such purified water or physiological saline so that the concentration is suitable for the intended purpose. Hereinafter, the reagent in this state is referred to as an LAL-bound bead reagent.

Next, actual detection or concentration measurement of endotoxin using the LAL-bound bead reagent in this example is described. In this example, there is described a case where the LAL reagent is further mixed in the above-mentioned LAL-bound bead reagent, and the reagent after mixing is blended with a test sample containing endotoxin. Note that, in the following description, it is assumed that an enzyme inhibitor is added when the above-mentioned LAL-bound bead reagent is prepared.

As described above, in a step of preparing the LAL-bound bead reagent, excess proteins in LAL or a coagulogen 3 purified from the proteins in LAL, which do not bind to the beads 1, are removed by washing. The serine protease which is adsorbed, supported, or bound to the beads 1 is inhibited irreversibly by addition of an enzyme inhibitor. Therefore, even if the LAL-bound bead reagent in this state is blended singly with a sample containing endotoxin, aggregation of the LAL-bound beads 10 may not occur.

Accordingly, in this example, the LAL-bound bead reagent is further mixed with the LAL reagent, and the mixture is blended with a sample containing endotoxin to aggregate the LAL-bound beads 10. By doing this, it is possible to supply protein components in LAL, such as serine proteases, to the LAL-bound bead reagent. By doing this, when the reagent is blended with a sample containing endotoxin, endotoxin can act more accurately on the serine protease in the reagent and a coagulogen can be hydrolyzed more accurately to form a coagulin. As a result, it is possible to aggregate the LAL-bound beads 10 more accurately and to measure endotoxin rapidly.

In this case, an effect of promoting aggregation of the LAL-bound beads 10 via the coagulin derived from the coagulogen in the LAL reagent supplied may also be obtained because the LAL reagent supplied contains the coagulogen.

In this example, even if the serine protease on the LAL-bound beads 10 is deactivated, an enzyme inhibitor which is irreversible and has a strong effect may be used when the LAL-bound bead reagent is prepared because excess serine protease is present in the LAL reagent to be mixed.

To improve convenience of measurement, the LAL-bound bead reagent prepared as above may be prepared by freeze-drying a defined amount of the LAL-bound bead reagent so that measurement can be performed only by adding a test sample. In this case, the freeze-dried LAL reagent may be mixed with the LAL-bound bead reagent freeze-dried in the same way as above at any rate, or a mixture obtained by the LAL-bound bead reagent and LAL reagent at any rate may be freeze-dried.

PRODUCTION EXAMPLE 1

Next, there is described an actual production example of a LAL-bound bead reagent obtained by binding polystyrene latex particles each having a carboxyl group on its bead surface to the LAL reagent under an environment where an irreversible enzyme inhibitor is added. As bead 1 having a carboxyl group on its surface, Polybead Calboxylate Microsphere (hereinafter, abbreviated as "PCM") with a particle size of 0.45 μm or 1.0 μm manufactured by Polysciences, Inc. was used.

As the LAL reagent, a reagent for detecting endotoxin manufactured by Wako Pure Chemical Industries, Ltd., Limulus HS-T Single Test Wako (hereinafter, abbreviated as "LAL reagent") was used. 1.0 mL of PCM was placed in a centrifugation tube with a maximum volume of 2.0 mL, and 0.1 M carbonate buffer (pH 9.6) was added up to the maximum volume. Then, the whole was mixed well and centrifuged using a desktop centrifuge at 12,500 rpm for 5 minutes to precipitate PCM, and the supernatant was removed. A series of procedures including blending with carbonate buffer, centrifugation, and removal of the supernatant were further repeated twice. Subsequently, 0.02 M phosphate buffer (pH 4.5) was added to PCM precipitated up to the maximum volume, and the whole was blended. Then, the procedures of centrifugation and removal of the supernatant were performed three times in total in the same way as above.

To the resultant PCM precipitates was added 0.75 mL of phosphate buffer used above, and 0.75 mL of a 2.0% aqueous solution of carbodiimide (water-soluble carbodiimide, manufactured by Dojindo Laboratories) was further added thereto, followed by stirring by turning upside down at room temperature for 3 hours to activate carboxyl groups on PCM. After the reaction, PCM was centrifuged to remove the supernatant and washed with phosphate buffer three times in the same way as above, and the final PCM precipitates were suspended in 0.5 mL of 0.2 M borate buffer (pH 8.5). Subsequently, the LAL reagent was dissolved in 0.25 mL of borate buffer to prepare two LAL reagent solutions, and the solutions were mixed with the PCM suspension to a volume of 1.0 mL. Moreover, a serine protease inhibitor, PMSF (phenylmethanesulfonyl fluoride), was added thereto so that the final concentration was 4 mM. The mixed solution was allowed to react at room temperature for 2 hours and then at 4° C. overnight so that the activated carboxyl groups on PCM in the mixed solution were bound to amino groups of each protein in LAL via amide bonds.

The mixed solution was centrifuged to remove the supernatant, and the residue was resuspended in 1.2 mL of borate buffer. To the solution was added 50 μL of 0.25 M 2-aminoethanol/borate buffer, and the solution was stirred by turning upside down at room temperature for 30 minutes to consume unreacted activated carboxyl groups on PCM with aminoethanol. Finally, the PCM suspension was centrifuged to obtain PCM precipitates, and the precipitates were washed three times in total by a series of procedures including resuspension in physiological saline for injection (manufactured by Otsuka Pharmaceutical Co., Ltd.), centrifugation, and removal of the supernatant, to thereby obtain an LAL-bound bead reagent.

MEASUREMENT EXAMPLE 1

Next, there is described Measurement Example 1 where the LAL-bound bead reagent obtained in Production Example 1 above was actually used. The LAL-bound bead reagent obtained in Production Example 1 was suspended in physiological saline for injection to 10 mL. Different amounts of the LAL-bound bead suspensions were mixed with water for injection (manufactured by Otsuka Pharmaceutical Co., Ltd.) to 100 μL. The resultant solutions were further mixed with the LAL reagent (Limulus HS-T Single Test Wako), and 100 μL of an aqueous endotoxin solution with a concentration of 2 EU/L was further added. The blended solution with a volume of 200 μL in total was placed in a dry-heat-sterilized (250° C., 5 hours) glass measurement cuvette having an outer diameter of 7 mm and internally equipped with a magnetic stirrer bar, and transmitted light intensity changes with time, caused by aggregation of the LAL-bound beads 10, were recorded using an apparatus for measuring platelet aggregation, PA-200 (manufactured by Kowa Company, Ltd.), capable of recording turbidity changes with time while stirring the sample.

Figure 2:
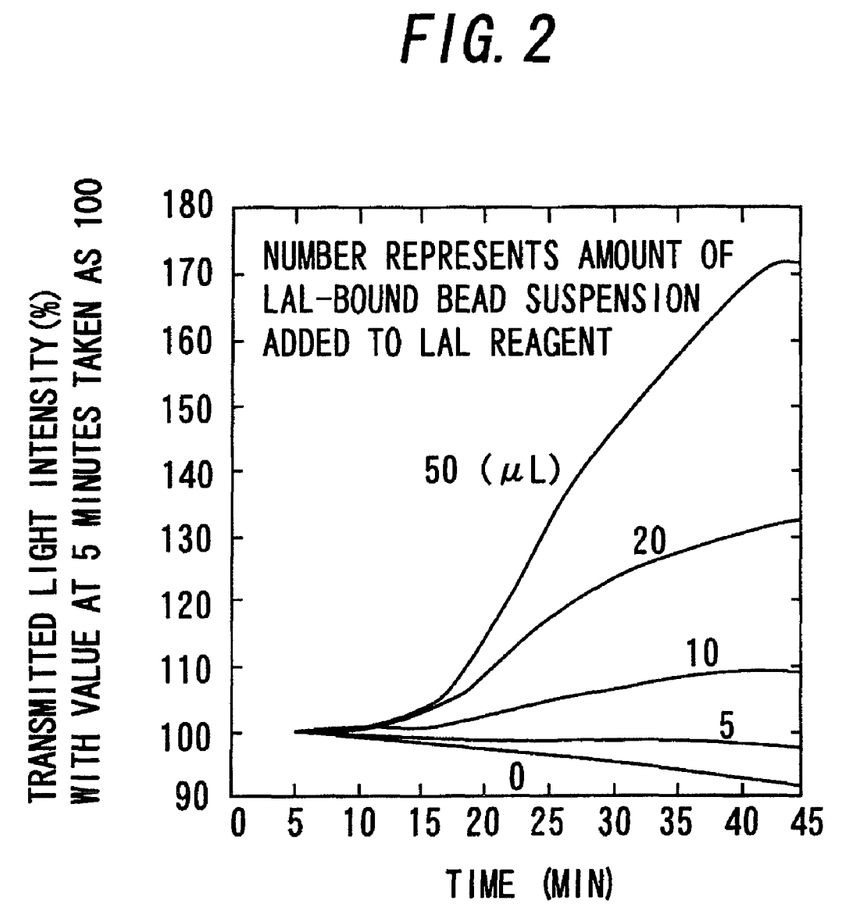
FIG. 2 is a graph illustrating a relationship between the amount of the LAL-bound beads and changes in transmitted light intensities in a blended solution obtained by blending the LAL-bound bead reagent of the present invention with a sample containing endotoxin.

FIG. 2 illustrates the transmitted light intensity changes with time, determined by the above-mentioned measurement. In FIG. 2, the horizontal axis shows the time, and the vertical axis shows the transmitted light intensities of the blended solutions. FIG. 2 illustrates the transmitted light intensity changes in the samples containing different amounts of the LAL-bound beads 10 with the transmitted light intensity determined 5 minutes after the start of stirring taken as 100% in the recorded data. FIG. 2 reveals that, as the amount of the LAL-bound beads 10 added becomes larger, the amount of the change becomes larger, and the aggregation starting time can be made earlier.

In the case where the LAL-bound bead reagent in this example is used for detection of endotoxin, for example, the sample may be judged to contain endotoxin when the transmitted light intensity in FIG. 2 reaches a predetermined value. In such a case, according to this example, as the amount of the LAL-bound beads 10 added becomes larger, the time for detection of endotoxin can be made shorter. Judgment of the sample to contain endotoxin when the transmitted light intensity in FIG. 2 reaches a predetermined value corresponds to detection of endotoxin by detection of formation of a gel in a blended solution.

MEASUREMENT EXAMPLE 2

Next, another measurement example where the LAL-bound bead reagent obtained in Production Example 1 is used is described. In this measurement, the LAL-bound bead reagent obtained in Production Example 1 was suspended in physiological saline for injection to 20 mL. 100 μL of the suspension was separated and mixed in the LAL reagent, and the mixture was further blended with 100 μL of aqueous solutions containing different concentrations of endotoxin so that the total volume was 200 μL. Then, in the same way as in Measurement Example 1 above, transmitted light intensity changes of the respective samples were recorded with the transmitted light intensity determined 5 minutes after the start of stirring taken as 100%.

Figure 3:
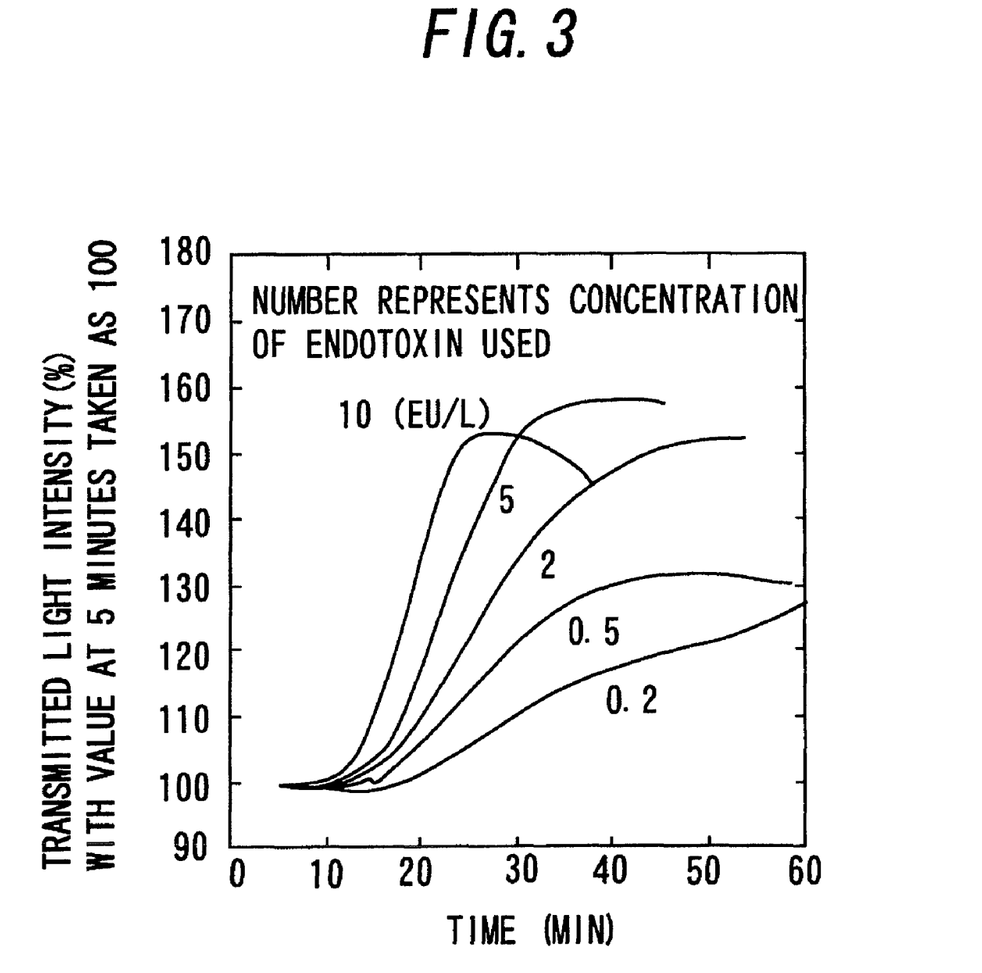
FIG. 3 is a graph illustrating a relationship between the concentration of endotoxin and changes in transmitted light intensities in a blended solution obtained by blending the LAL-bound bead reagent of the present invention with a sample containing endotoxin.

FIG. 3 illustrates the transmitted light intensity changes with time, determined by this measurement. In FIG. 3, the horizontal axis shows the time, and the vertical axis shows the transmitted light intensities of the blended solutions. As shown in FIG. 3, as the concentration of endotoxin added to the sample becomes large, the transmitted light intensities increase more exponentially, resulting in reducing the aggregation starting time. That is, in the case where the LAL-bound bead reagent in this example is used for measurement of the concentration of endotoxin, for example, the concentration measurement can be performed based on the time taken until the transmitted light intensity reaches a predetermined value (aggregation starting time) in FIG. 3. This corresponds to measurement of the concentration of endotoxin by measuring the degree of gel formation.

Figure 4:
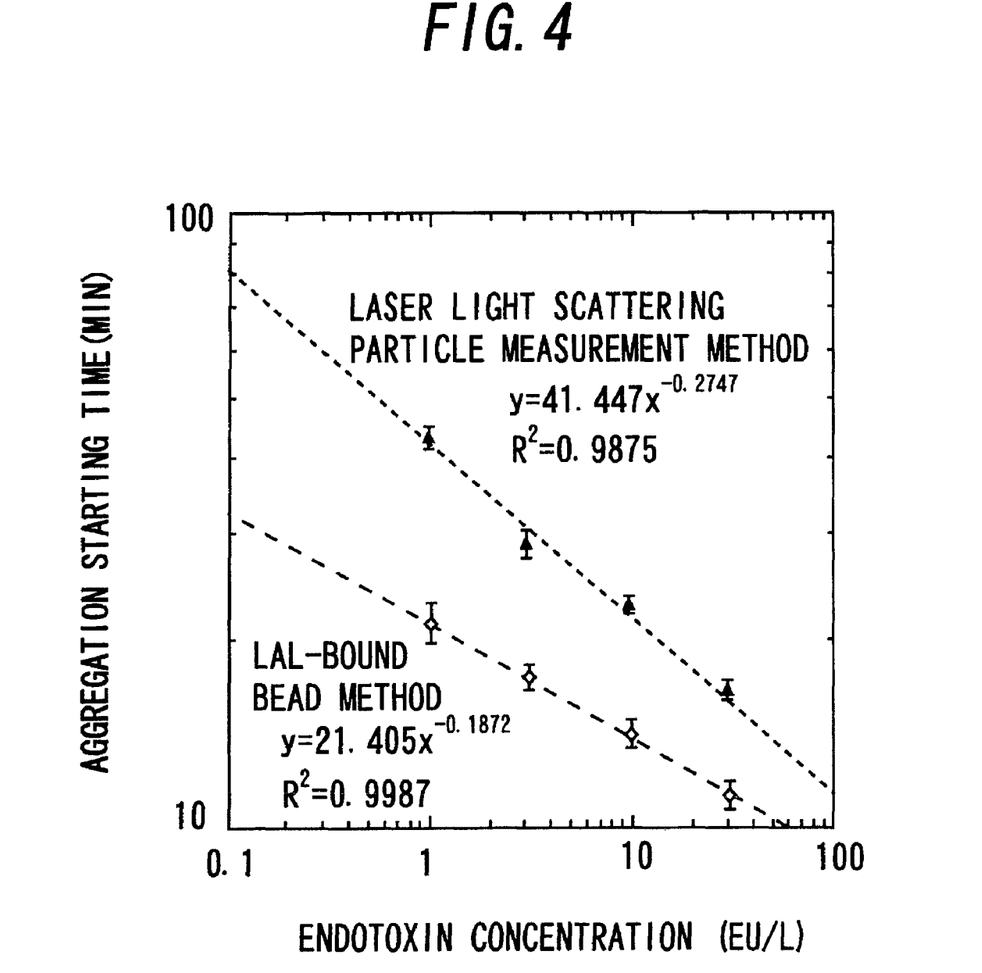
FIG. 4 is a graph for comparing a relationship between the endotoxin concentration and the gel aggregation starting time in a reaction between proteins in LAL and endotoxin in the case of using the LAL-bound bead method and that in the case of using the laser light scattering particle measurement method.

Next, the relationship between the concentration of endotoxin and the aggregation starting time, determined as above, was compared with the relationship between the concentration of endotoxin and the aggregation starting time, determined by the laser light scattering particle measurement method in the case where no LAL-bound beads 10 were used. FIG. 4 illustrates the results of the comparison. As shown in FIG. 4, in the case of using the LAL-bound beads 10 (in FIG. 4, referred to as "LAL-bound bead method" for the purpose of simplification), although the turbidimetric method was used, the aggregation starting time is earlier than that in the case of using the laser light scattering particle measurement method. This reveals that use of the LAL-bound beads 10 enables rapid detection of endotoxin compared with the case of the laser light scattering particle measurement method.

Note that, in Production Example 1 in this example, proteins in LAL was bound to the beads 1 without selection to prepare the LAL-bound bead reagent. However, as in the case of this example, in the case where the LAL-bound beads 10 are aggregated by further mixing the LAL-bound bead reagent with the LAL reagent and blending the mixture with a sample containing endotoxin, the coagulogen is desirably adsorbed, supported, or bound as many as possible on the beads 1 used for formation of the LAL-bound beads 10. Therefore, when the LAL-bound beads 10 are prepared, a purified coagulogen may be adsorbed, supported, or bound to the beads 1 rather than binding proteins in LAL on the beads 1 without selection.

As in the case of this example, in the case where proteins in LAL are adsorbed, supported, or bound to the beads 1 without selection to prepare the LAL-bound bead reagent, at least one kind of enzyme inhibitor and at least one kind of iron ion or aluminum ion having an effect of reducing the functions of endotoxin itself may be made to exist together, so as to inhibit hydrolysis of the coagulogen into the coagulin. Alternatively, at least one kind of iron ion or aluminum ion may be added singly.

In the above-mentioned example, turbidity changes with time were measured while stirring a blended solution obtained by mixing the LAL-bound bead reagent with the LAL reagent and blending an aqueous endotoxin solution therein. However, the stirring of the blended solution is not always necessary. When the turbidity changes with time are measured while the blended solution is not stirred and left to stand, rapid measurement of endotoxin may be performed by using the LAL-bound bead reagent.

In the above-mentioned example, gel formation (formation of aggregates obtained by association of the LAL-bound beads 10) may be measured by the laser light scattering particle measurement method while stirring a blended solution obtained by mixing the LAL-bound bead reagent with the LAL reagent and blending an aqueous endotoxin solution therein. By doing this, a synergistic effect of the LAL-bound bead method and the laser light scattering particle measurement method may enable more rapid measurement of endotoxin.

EXAMPLE 2

Next, Example 2 in the present invention is described. In this example, an example of blending the LAL-bound bead reagent singly with a test sample containing endotoxin before use is described.

In the case where the LAL-bound bead reagent is mixed singly with a test sample containing endotoxin before use, endotoxin can be measured more simply because a step of mixing the LAL-bound bead reagent with the LAL reagent can be omitted. However, in this case, proteins in LAL cannot be supplemented to the LAL-bound bead reagent because the LAL reagent cannot be further added to the LAL-bound bead reagent.

Therefore, in this case, both the coagulogen and serine protease are desirably adsorbed, supported, or bound to the LAL-bound beads 10. By doing this, endotoxin can act on the serine protease in the LAL-bound bead reagent by blending the LAL-bound bead reagent singly with a sample containing endotoxin without further mixing the LAL-bound bead reagent with the LAL reagent. This can cause hydrolysis of the coagulogen in the LAL-bound bead reagent into the coagulin, and as a result, the LAL-bound beads 10 in the LAL-bound bead reagent can be associated to aggregate at an early stage.

As described above, in this example, when the LAL-bound bead reagent is prepared, proteins in LAL are desirably adsorbed, supported, or bound to the surfaces of the beads 1 instead of adsorbing, supporting, or binding only purified coagulogen to the surfaces of the beads 1.

Next, in this example, there is described the case where the coagulogen and a protein component other than the coagulogen in LAL, such as the serine protease, are bound to the beads 1. Even in such a case, in this example, when the serine protease activity is inhibited irreversibly by an enzyme inhibitor added in a process of preparation of the LAL-bound bead reagent, the LAL-bound beads 10 may not be aggregated even if the LAL-bound bead reagent is blended with a sample containing endotoxin.

Therefore, in this example, it is desirable to select an enzyme inhibitor or a preparation method, which does not inhibit irreversibly enzymatic functions or does not deactivate the enzyme. For example, in the process of preparation of the LAL-bound bead reagent, an excessive amount of iron ion or aluminum ion may be added to reduce the effect of endotoxin, resulting in preventing hydrolysis of the coagulogen into the coagulin without inhibiting the enzymatic functions. Further, in the process of preparation of the LAL-bound bead reagent, for example, the activity of the serine protease may be inhibited by a not-irreversible enzyme inhibitor (reversible inhibitor). In this case, the deactivation of the enzyme may be terminated by washing.

By doing this, it is possible to suppress irreversible inhibition of the enzymatic functions or deactivation of the protein in LAL, which is adsorbed, supported, or bound to the beads 1. As a result, endotoxin can be measured sensitively by blending with a sample containing endotoxin without further mixing the LAL reagent with the LAL-bound bead reagent.

Note that the LAL-bound reagent prepared in examples above corresponds to the reagent kit for endotoxin measurement of the present invention.

What is claimed is:

1. A method of measuring endotoxin for detecting endotoxin in a sample or measuring the concentration of endotoxin in a sample, comprising:
    binding or adsorbing a predetermined protein, which is a serine protease and/or a coagulogen, in a limulus amoebocyte lysate to surfaces of fine particles capable of dispersing in a reagent;
    blending the reagent where the fine particles to which the predetermined protein is bound or adsorbed are dispersed with said sample; and
    detecting formation of a gel in the blended solution of the reagent and the sample to detect endotoxin or measuring the degree of formation of the gel to measure the concentration of endotoxin.

2. The method of measuring endotoxin according to claim 1, wherein the predetermined protein is a coagulogen purified from the limulus amoebocyte lysate.

3. The method of measuring endotoxin according to claim 1, comprising:
    further mixing the reagent where the fine particles to which the predetermined protein is bound or adsorbed are dispersed with the limulus amoebocyte lysate; and
    blending the reagent and the sample simultaneously with or after the mixing.

4. A reagent kit for measurement of endotoxin, comprising fine particles prepared by binding or adsorbing a predetermined protein, which is a serine protease and/or a coagulogen, in a limulus amoebocyte lysate to surfaces of said fine particles capable of dispersing in a reagent.

5. The reagent kit for measurement of endotoxin according to claim 4, wherein the predetermined protein is a coagulogen purified from the limulus amoebocyte lysate.

6. The reagent kit for measurement of endotoxin according to claim 4, wherein:
    the predetermined protein includes serine protease and a coagulogen; and
    an inhibitor which inhibits a reaction between the serine protease and endotoxin is further added to the reagent where the fine particles to which the predetermined protein is bound or adsorbed are dispersed.

7. The reagent kit for measurement of endotoxin according to claim 4, wherein the kit is prepared by further mixing the reagent where the fine particles to which the predetermined protein is bound or adsorbed are dispersed with the limulus amoebocyte lysate.

8. The method of measuring endotoxin according to claim 2, comprising:
    further mixing the reagent where the fine particles to which the predetermined protein is bound or adsorbed are dispersed with the limulus amoebocyte lysate; and
    blending the reagent and the sample simultaneously with or after the mixing.

9. The reagent kit for measurement of endotoxin according to claim 5, wherein the kit is prepared by further mixing the reagent where the fine particles to which the predetermined protein is bound or adsorbed are dispersed with the limulus amoebocyte lysate.

10. The reagent kit for measurement of endotoxin according to claim 6, wherein the kit is prepared by further mixing the reagent where the fine particles to which the predetermined protein is bound or adsorbed are dispersed with the limulus amoebocyte lysate.

* * * * *

UNITED STATES PATENT AND TRADEMARK OFFICE
CERTIFICATE OF CORRECTION

PATENT NO. : 8,211,651 B2  
APPLICATION NO. : 12/809337  
DATED : July 3, 2012  
INVENTOR(S) : Katsumi Yabusaki Page 1 of 1

It is certified that error appears in the above-identified patent and that said Letters Patent is hereby corrected as shown below:

Column 10, Line 18, "Polybead Calboxylate" should be changed to --Polybead Carboxylate--

Signed and Sealed this  
Fifth Day of February, 2013

Teresa Stanek Rea  
*Acting Director of the United States Patent and Trademark Office*